(12) United States Patent
McNair

(10) Patent No.: US 10,213,145 B1
(45) Date of Patent: Feb. 26, 2019

(54) CONTEXT-AWARE POST TRAUMATIC STRESS DISORDER MONITORING AND INTERVENTION

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 132 days.

(21) Appl. No.: 15/284,463

(22) Filed: Oct. 3, 2016

Related U.S. Application Data

(60) Provisional application No. 62/236,128, filed on Oct. 1, 2015.

(51) Int. Cl.
*A61B 5/16* (2006.01)
*A61B 5/024* (2006.01)
*A61B 5/0245* (2006.01)
*A61B 5/04* (2006.01)
*A61B 5/0464* (2006.01)
*A61B 5/00* (2006.01)

(52) U.S. Cl.
CPC ............ *A61B 5/165* (2013.01); *A61B 5/0245* (2013.01); *A61B 5/02405* (2013.01); *A61B 5/02416* (2013.01); *A61B 5/04017* (2013.01); *A61B 5/0464* (2013.01); *A61B 5/7278* (2013.01)

(58) Field of Classification Search
CPC . A61B 5/165; A61B 5/02405; A61B 5/02416; A61B 5/0245; A61B 5/04017; A61B 5/0464; A61B 5/7278
See application file for complete search history.

(56) References Cited

U.S. PATENT DOCUMENTS

2003/0163057 A1* 8/2003 Flick .................... A61B 5/7275
600/509
2005/0004608 A1* 1/2005 Bullinga ............... A61N 1/3702
607/9
2009/0292180 A1* 11/2009 Mirow .................. G16H 10/20
600/301

(Continued)

*Primary Examiner* — Catherine Voorhees
*Assistant Examiner* — Natasha Patel
(74) *Attorney, Agent, or Firm* — Shook, Hardy & Bacon L.L.P.

(57) ABSTRACT

Optimizing psychiatric and physiologic monitoring of a patient having PTSD or anxiety-related mental health condition. According to an embodiment, one or more physiological variables are longitudinally measured; resting heart rate is measured from which a timeseries is constructed; outlier anomalous values are removed from the timeseries, it is de-trended and/or de-meaned; and a serial normal sinus rhythm beats (SDNN) and/or other parameters are determined. Fractal properties of the serial SDNN values are calculated, such as the Hurst exponent alpha via detrended fluctuation analysis (DFA) or spectral regression; and other measures of chaos and nonlinearity are calculated, such as the Shannon entropy of the SDNN or related timeseries. Where such measures indicate a statistically-significant transgression of a context-indexed reference range, a notification is provided to a case management clinician or caregiver so that appropriate additional evaluation and diagnosis and treatment may be undertaken.

20 Claims, 11 Drawing Sheets

(56) References Cited

U.S. PATENT DOCUMENTS

| | | | |
|---|---|---|---|
| 2011/0202486 A1* | 8/2011 | Fung | G16H 50/20 |
| | | | 706/12 |
| 2012/0232414 A1* | 9/2012 | Mollicone | A61B 5/024 |
| | | | 600/508 |
| 2012/0238800 A1* | 9/2012 | Naujokat | A61B 5/0402 |
| | | | 600/26 |
| 2014/0179270 A1* | 6/2014 | Anand | H04W 12/12 |
| | | | 455/410 |
| 2014/0330159 A1* | 11/2014 | Costa | A61B 5/1124 |
| | | | 600/558 |

* cited by examiner

Example PTSD screening instrument (CAPS)

FIG. 3.

HRV VALUES FROM
64-DAY SERIES OF 5-MIN A.M. RESTING RR RECORDINGS

| PARAMETER | VALUE | UNITS |
|---|---|---|
| $\overline{RR}$ | 0.798 | SEC |
| $\overline{HR}$ | 75.2 | BPM |
| SDNN | 0.145 | SEC |
| SDNN HURST EXPONENT (ALPHA) | 0.288 | - |
| SDNN ENTROPY (CHAO-SHEN) | 1.44 | - |

FIG. 5.

```
################################################################

# HRV variability by detrended fluctuation analysis and spectral regression

########################################################## library(fractal)
library(entropy)
library(tsoutliers)

# load beatregister containing 64 consecutive days' 5-min (360-beat segments, 500 Hz sampling)
resting seated ECG beat data from one individual
beats <- read.csv(file="c:/0_cerdsm/0__math_models/7_behavioral/ptsd/beatreg.csv", header=TRUE)
beat.len.m1 <- length(beats$beat) - 1 convert to 23,040 RR intervals
rr <- rep(NA, beat.len.m1)
for (i in 1:beat.len.m1) {
  rr[i] <- beats$beat[i+1] - beats$beat[i]
} calculate overall properties of the 64-day record
mean(rr)
min(rr)
max(rr)
sd(rr)
plot(seq(1:beat.len.m1),rr,type="l")

# initialize SDNN array
sdnn <- rep(0,64)

# extract each day and calculate SDNN array
k <- 1
for (i in 1:64) {
  sdnn[i] <- sd(rr[k:(k+359)])
  k <- k + 360
} plot SDNN values
hist(sdnn)
plot(seq(1:64),sdnn,type="l", lwd=2, col="red")

# calculate DFA scaling exponent of SDNN time series
DFA.sdnn <- DFA(sdnn, detrend="poly1", sum.order=0, overlap=0.8)

# extract multiscale regression coefficient
h.dfa <- attr(DFA.sdnn,"logfit")[1]$coefficients[2] # Hurst exponent (alpha; slope)
h.dfa
                        .
                        .
                        .
```

CONTINUES IN FIG. 6B

*FIG. 6A.*

CONTINUES FROM FIG. 6A

.
.
.

```
# compare to Hurst exponent by spectral regression
h.spec <- hurstSpec(sdnn, method="smoothed", sdf.method="multitaper")
h.spec monofractal H < 0.7 (vs. multifractal H >= 0.7)

display results
print(DFA.sdnn)

# plot summary of DFA results
eda.plot(DFA.sdnn)

# determine Priestley-Subba Rao stationarity of multi-day patterns
stationary <- stationarity(sdnn, n.block=4)
stationary evaluate whether time series is deterministic
determ <- determinism(sdnn, olag=1)
determ identify timeseries outliers identified by ARIMA regression and replace them with median SDNN value
med <- median(sdnn)
fit <- arima(sdnn, order=c(1,1,0), seasonal=list(order=c(2,0,2)))
res <- locate.outliers.oloop(sdnn, fit, types=c("AO","LS","TC"))
res$outliers
out <- remove.outliers(res, sdnn, method="bottom-up", tsmethod.call=fit$call)$outliers
len.out <- length(out$ind)
for (i in 1:len.out) {
  j <- out$ind[i]
  sdnn[j] <- med
} single high outlier out$ind[1] == 31 replaced discretize into 5 categories
sdnn.disc <- discretize(sdnn, numBins=5)

# determine whether discretization of SDNN values as counts in equal-width bins is adversely affected
by outliers calculate entropy by one or more methods
entropy(sdnn.disc, method="ML")
entropy(sdnn.disc, method="MM")
entropy(sdnn.disc, method="Jeffreys")
entropy(sdnn.disc, method="Laplace")
entropy(sdnn.disc, method="SG")
entropy(sdnn.disc, method="minimax")
entropy(sdnn.disc, method="CS")
```

*FIG. 6B*

```
###############################################################

# PTSD multivariate imputation by chained equations (mice) and spectral regression

######################################################### library(methods)
library(Rcpp)
library(lattice)
library(MASS)
library(nnet)
library(randomForest)
library(rpart)
library(mice)

# each variable has its own imputation model
# built-in imputation models are provided for continuous data (predictive mean matching, normal),
# binary data (logistic regression), categorical data (polytomous regression), and
# ordinal data (proportional odds)
CAPS variables are ordinal so prop odds model is used for each of these load data.frame of 52 observations of CAPS data
data(fdd)
str(fdd)

# display missing data patterns as binary 2D array; 28 of 52 rows have some missing cells
ptsd <- md.pattern(fdd)
str(ptsd)

# impute 5-fold (indexed by column_1 .imp) with proportional odds for 0-4 CAPS scores on 30 variables
imp <- mice(fdd, print=FALSE, defaultMethod="polr", maxit=5)

# list the actual imputations for homicidality variable
imp$imputations$homic fill in the missing data, and return the completed data
fdd <- complete(imp, action="long", include=TRUE)[, -2]
```

*FIG. 6C*

CONTEXT-AWARE POST TRAUMATIC STRESS DISORDER MONITORING AND INTERVENTION

CROSS-REFERENCE TO RELATED APPLICATIONS

This application claims priority to U.S. Provisional Patent Application No. 62/236,128 filed Oct. 1, 2015, and titled "Context-Aware Post Tramatic Stress Disorder Monitoring and Intervention," the contents of which is incorporated herein by reference in its entirety.

BACKGROUND

Traumatic injury is one of the most common traumatic events worldwide, accounting for approximately 9% of global mortality. Reported rates of post-traumatic stress disorder (PTSD) within the first 6 months of injury range between 10% and 20% in civilian populations and are substantially higher in military personnel returned from combat. Early interventions (such as education or psychological debriefing) for persons exposed to traumatic events have very low success in preventing PTSD, whereas there is evidence that early treatment of acute PTSD with prazosin or other medications or trauma-focused cognitive behavioral therapy can prevent progression to a chronic course of PTSD. Thus, there is great interest in reliable means to identify which persons merit such early treatments, and to longitudinally monitor the evolving status of persons at-risk of developing PTSD or under treatment for PTSD.

There are many challenges to the identification of valid, reliable biomarkers for diagnosing PTSD and assessing its severity. Although many biological abnormalities have been found to be associated with PTSD, including endocrine and neurobiological alterations, there is significant variability in these. PTSD is a multifaceted psychological disorder with symptoms across four psychiatric symptom clusters, and its typology exhibits multiple, distinct longitudinal trajectories encompassing heterogeneous phenotypes. Furthermore, biological (genetic, epigenetic, endocrine, immunological, neurological), environmental (causation and developmental timing of trauma), psychological (cognitive, emotional, behavioral), and social vulnerability factors likely interact in complex ways to affect the risk for PTSD. Given the diagnostic heterogeneity of PTSD and its multifactorial etiology, it is unlikely that a single biomarker will be identified.

Nonetheless, the combination of traditional survey-type questionnaire screening instruments with physiological measures acquired noninvasively via wearable sensors offers promise for higher accuracy. Primary challenges to be confronted involve minimizing stigmatization of the individual being monitored, promoting longitudinal compliance with the monitoring, and arranging signal-processing that achieves useful timeliness and responsiveness to changes in the individual's evolving condition while simultaneously avoiding an excessive rate of false-alarm or Type I errors.

SUMMARY

Systems, methods and computer-readable media are provided for optimizing psychiatric and physiologic monitoring of a subject who has, or is thought to be at risk of, PTSD or other anxiety-related mental health condition. Data may be collected and analyzed assess the mental health and cardiac electrophysiologic status and autonomic parasympathetic/sympathetic balance of human and/or animal subjects. In particular, in one embodiment, one or more biomarkers for PTSD are longitudinally measured using clinician-administered or self-reported survey instruments or laboratory tests; measuring resting heart rate at least daily, preferably in the morning hours and preferably for 5 to 10 minutes; constructing a timeseries from said measurements; removing timeseries outlier anomalous values from the timeseries; de-trending and de-meaning the series; calculating serial normal sinus rhythm beats (SDNN) and/or other parameters, such as ordinarily comprise determinations of HRV; calculating fractal properties of the serial SDNN values, such as the Hurst exponent alpha via detrended fluctuation analysis (DFA) or spectral regression; calculating other measures of chaos and nonlinearity, such as the Shannon entropy of the SDNN or related timeseries; and, if such measures indicate a statistically-significant transgression of a context-indexed reference range, notifying case management clinicians so that appropriate additional evaluation and diagnosis and treatment may be undertaken.

Some embodiments, may be used in conjunction with existing clinician-administered or self-reported survey instruments that establish an interpretive context in terms of ascertaining the subject's risk for developing PTSD, determining the current presence or absence of PTSD in the subject, or estimating the severity of PTSD that has already materialized in the subject. Moreover, the context provided by the survey instrument data affords improved sensitivity and specificity of decision-levels for heart rate variability (HRV) parameters with regard to diagnosis and management of PTSD. Conversely, the HRV data enables multi-variable imputation of any missing item values in survey instrument information with improved context-specific accuracy.

BRIEF DESCRIPTION OF THE DRAWINGS

The present invention is described in detail below with reference to the attached drawing figures, wherein:

FIG. 3 depicts one example of a PTSD screening instrument, in accordance with an embodiment of the disclosure;

FIG. 5 illustratively depicts HRV values from the example data provided in connection to FIGS. 4A-4C; and FIGS. 6A-6C illustratively provide an example embodiment of a computer program routines used for context-aware PTSD monitoring, in accordance with an embodiment of the disclosure.

DETAILED DESCRIPTION

Figure 1A:
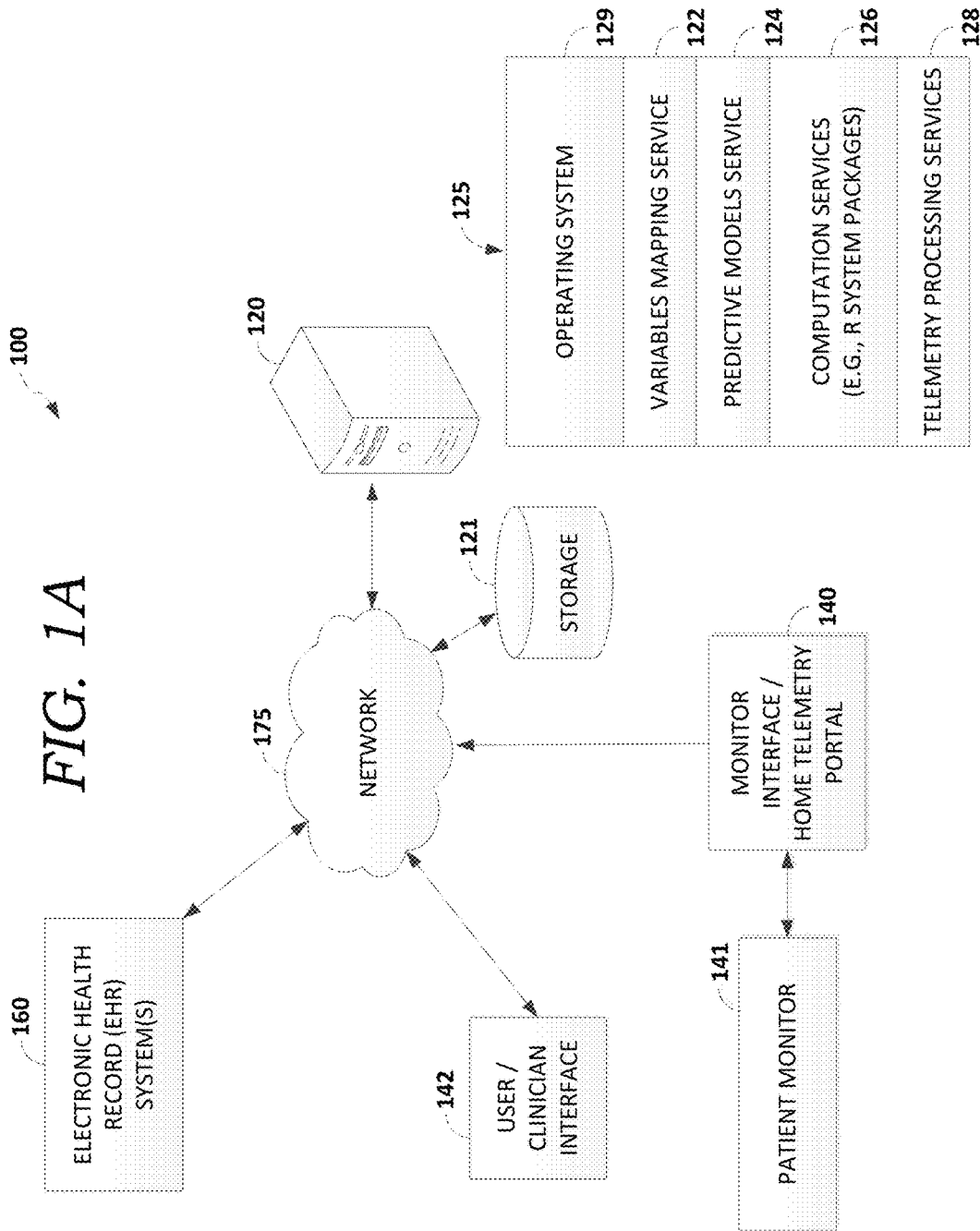
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Accordingly, at a high level, this disclosure describes, among other things, methods and systems, for identifying persons having PTSD who may need intervention from a caregiver based on context-aware PTSD monitoring. In one embodiment, this includes collecting daily 5- to 10-minute RR cardiac beat timeseries, which may be de-trended and de-meaned, in some embodiments, to remove the effects of drift and location. Standard HRV parameters may be calculated from each day's timeseries, including the standard deviation of NN intervals (SDNN) in seconds. A plurality of days' values may be used to calculate Hurst exponent alpha, entropy, and, in some embodiments, other metrics of scale-dependence, stationarity, nonlinearity, and chaotic properties of the multi-day timeseries. The resulting values then may be indexed according to standard clinician-administered or self-reported survey instrument's scores, so as to establish context-aware normative reference values for the SDNN, Hurst exponent, entropy, and other measures. Based on this, if departure of the subject's measures from normative reference values has occurred, then the condition is deemed to be a true-positive and notification to a caregiver is provided. If no departure from context-aware normative reference values has occurred then no alarm or notification is emitted.

As described previously, some embodiments of the disclosure can be used in conjunction with existing prior art clinician-administered or self-reported survey instruments that establish an interpretive context in terms of ascertaining the subject's risk for developing PTSD, determining the current presence or absence of PTSD in the subject, or estimating the severity of PTSD that has already materialized in the subject. The context provided by the survey instrument data affords improved sensitivity and specificity of decision-levels for heart rate variability (HRV) parameters with regard to diagnosis and management of PTSD. Conversely, the HRV data enables multi-variable imputation of any missing item values in survey instrument information with improved context-specific accuracy. Embodiments of the invention may incorporate methods from the fields of digital signal processing (DSP), nonlinear timeseries analysis, and data analysis of the fractal and entropic properties of a daily resting heart rate timeseries signal to detect and ascertain quantitative longitudinal changes in the context of biomarkers used to screen for and manage post-traumatic stress disorder (PTSD) or other anxiety-related psychiatric conditions.

As described above, there is great interest in reliable means to identify which persons merit intervention for PTSD and to monitor the evolving status of persons at-risk of developing PTSD or under treatment for PTSD. Following exposure to injury or trauma or violence, PTSD symptoms often emerge slowly or insidiously over a period of weeks or months, after a latency period or after an interval during which no access of health services occurs. Accordingly, there is a need for technologies that are non-stigmatizing and that can facilitate earlier identification of individuals exposed to injury or returning from combat who are developing signs of PTSD.

For example, in U.S. soldiers returning from combat, at 1 month approximately 4% of the soldiers had probable PTSD and depression; at 4 months, 12.2% had PTSD and 8.9% had depression; at 7 months, 12.0% had PTSD and 9.3% had depression. In the longitudinal cohort, 78.8% of those positive for PTSD or depression at 7 months had screened negative for both conditions at 1 month. This indicates that single-determination "snapshot" assessment at any point in time is prone to yield false-negative results, leading to under-recognition and under-treatment of significant PTSD.

As an alternative to clinician-administered assessments, it might be thought that self-reporting by patients would offer advantages. However, even though monitoring via self-reporting has a strong theoretical foundation and may be key to more structured treatments for PTSD, frequent monitoring by survey instruments is intrusive and may itself exacerbate the subject's stress symptoms. Furthermore, patients' compliance with monitoring by self-reporting is typically low, which complicates the interpretation and gives rise to a high false-negative error rate, delaying proper care or prevention.

Additionally, it is common that many subjects exhibit varying sensitivity regarding providing responses to different PTSD survey questions. Thus, partial survey completion leaving various items without responses is a frequent occurrence. Typically, such data are 'missing-not-at-random' (MNAR) in the statistician's sense, which is why chained-equations or random forest (RF) methods and related robust multiple imputation techniques are needed to adequately mitigate the non-random causes of missingness. While items in the CAPS-1 and other surveys are all of ordinal data type, they exhibit markedly different distributions of values as well, which is why multiple imputation methods that allow divergent imputations to prevail for different items are important.

While PTSD-associated decrease in overall HRV (especially the standard deviation of serial normal sinus rhythm beats, or SDNN) and decreased variability of serial HRV values by detrended fluctuation analysis (DFA) have been reported in previous studies, these measures exhibit considerable day-to-day within-subject variability. As such, when single determinations of these are used as "snapshot" indicators they tend to produce an excessive rate of Type 1 statistical error, suggesting significant change when in fact there has been no such change.

The circadian cycle of HRV values has also been studied recently. Overall, high-frequency (HF) spectral power (a marker of autonomic parasympathetic modulation) gradually increases from the late afternoon, reaches peak amplitude around 3 a.m., and then decreases throughout the daytime until late afternoon. In contrast, obesity had adverse effects on all circadian parameters. The age, sex and race showed varying differences on the circadian parameters. These various factors must be addressed in any reliable use of HRV metrics for evaluation of PTSD.

Heart rate variability may be analyzed conventionally with time and frequency domain methods that measure the overall magnitude of consecutive-beat RR interval fluctuations around its mean value or the magnitude of fluctuations in some predetermined frequencies. Analysis of heart rate dynamics by methods based on chaos theory and nonlinear system theory has gained recent interest. This interest is based on observations suggesting that the mechanisms involved in cardiovascular regulation likely interact with each other in a nonlinear way. Furthermore, recent observational studies suggest that some indexes describing non-linear heart rate dynamics, such as fractal scaling exponents, may provide more powerful prognostic information than the traditional heart rate variability indexes. In particular, the short-term fractal scaling exponent measured by the detrended fluctuation analysis method has predicted fatal cardiovascular events in various populations. Approximate entropy, a nonlinear index of heart rate dynamics, that describes the complexity of RR interval behavior, has provided information on the vulnerability to atrial fibrillation. Many other nonlinear indexes—for example Lyapunov exponent and correlation dimensions—also give information on the characteristics of heart rate dynamics, but their clinical utility is not yet well established.

Traditionally, resting HRV parameters were measured from 24-hour Holter electrocardiogram (ECG) recordings. This was an historical consequence of practices from an era when Holter monitoring was performed for reasons such as detection of intermittent arrhythmias. To this day, it is still uncommon for cardiologists or other physicians to order a determination of HRV. Indeed, unless there is an arrhythmia present or moderate to severe heart failure or other condition, 24-hour ECG monitoring is not routinely part of a cardiological assessment. In recent years, however, an increasing number of conditions have been noted to exhibit abnormally reduced HRV values. Some of these require characterization of circadian (night-day) variations in HRV, in which 24-hour monitoring is important, but in many other conditions the HRV features during ordinary waking hours exhibit changes that are sufficient for diagnostic or theranostic or predictive purposes. Shorter time-interval recordings (such as 5 minutes to 10 minutes) and recording during ordinary waking hours are important in terms of facilitating patients' compliance with data collection and in terms of favoring a variety of filtering or sampling methods to exclude recorded intervals in which ECG artifacts were present or performance of physical activity occurred or other censorable events transpired that would impair the accuracy of determinations of HRV parameters.

Accordingly, some embodiments of the disclosure are directed to systems and methods for optimizing psychiatric and physiologic monitoring of a subject who has, or is thought to be at risk of, PTSD or other anxiety-related mental health condition. In one embodiment, one or more biomarkers of PTSD are longitudinally measuring using clinician-administered or self-reported survey instruments or laboratory tests; measuring resting heart rate at least daily, preferably in the morning hours and preferably for 5 to 10 minutes; a timeseries may be constructed from said measurements, which may include removing timeseries outlier anomalous values from the timeseries and/or de-trending and de-meaning the series. The SDNN and other parameters such as ordinarily comprise determinations of HRV are determined, which may include fractal properties of the serial SDNN values, such as the Hurst exponent alpha via detrended fluctuation analysis (DFA) or spectral regression. Other measures of chaos and nonlinearity may also be determined, in some embodiments, such as the Shannon entropy of the SDNN or related timeseries. Where such measures indicate a statistically-significant transgression of a context-indexed reference range, a case management clinician or caregiver may be notified so that appropriate additional evaluation and diagnosis and treatment may be undertaken.

An ideal theranostic apparatus for predicting, diagnosing, and longitudinally managing PTSD should detect all situations that require prompt attention (low false-negative rate) and ascertain such situations quickly, without the elapsing of very many days before a signal for intervention is emitted. In addition, an ideal apparatus should only detect hazards or conditions that require prompt attention (low false-positive rate), to avoid stigmatizing the subject or causing excessive intrusions such as would lead to withdrawal of assent or noncompliance on the part of the subject. In other words, the statistical sensitivity and specificity should both be as high as possible, preferably close to 100%. Beyond this, an ideal monitoring apparatus for longitudinal prevention, detection, and management of PTSD would meet the following goals, provided by some embodiments of the disclosure: (a) Able to accurately detect clinically significant change in status or in response to treatment with less than 30 days lead-time; (b) Able to be repeated frequently ad lib, with little inconvenience or invasiveness and low incremental cost associated with repeat measurements; (c) Integration with existing prior art assessment instruments such as CAPS-1 or SPAN or TSQ; and (d) Context-specificity to the traumatic event-type and severity; the individual's age, gender, socioeconomic background, and civilian/military setting.

Other efforts at this have been aimed at improving detection of PTSD and measurement of its severity. Despite these advances, these approaches continues to have several limitations, including: (1) Excessively time-consuming, such that it is impracticable to obtain frequent, repeated measurements that are required for close monitoring and rapid response to changes in status; (2) Excessive false-negative rate, especially for self-reported data where the subject may be reluctant to disclose certain signs or symptoms that denote illness, weakness, or worsening condition; (3) Excessive false-positive rate, especially for single-episode heart rate variability measurements where postural effects or circadian variations or intermittent differences in the length of or circumstances of recording ECG or plethysmographic beat register information yield transiently abnormal values that are not representative of the subject's predominant condition or trends; (4) Excessive invasiveness or expense associated with laboratory tests such as cerebrospinal fluid chemistries, gene-expression assays, or fMRI or PET imaging of the brain; or (5) Requirement for prolonged and fastidious collection of day-night data, such as sleep actigraphy.

Accordingly, it is therefore valuable that some embodiments of the disclosure ameliorate these limitations and providing objective, quantitative means for automatically determining PTSD status by means that are non-stigmatizing and true-positive interpretations to be promptly emitted without undue delay.

Referring now to the drawings in general, and initially to FIG. 1A in particular, an aspect of an operating environment 100 is provided suitable for practicing an embodiment of our invention. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of the invention including collecting and analyzing unstructured text data from electronic health record(s) to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, ambulatory clinic EHR systems, psychiatry/neurology EHR systems, and may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors, for example.

Although FIG. 1A depicts an exemplary EHR system 160, it is contemplated that an embodiment relies on monitor interface/home telemetry portal 140 and/or patient monitor 141 for storing and retrieving patient record information such as information acquired from monitor 141.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient or set of patients for which the likelihood(s) of future events such as acute risk of deterioration are determined according to the embodiments presented herein. Embodiments of interface 142 also facilitates accessing and receiving information from a user or health care provider about a specific patient or population of patients including patient history; health care resource data; variables measurements, timeseries, and predictions (including plotting or displaying the determined outcome and/or issuing an alert) described herein; or other health-related information, and facilitates the display of results, recommendations, or orders, for example. In an embodiment, interface 142 also facilitates receiving orders for the patient from the clinician/user, based on the results of monitoring and predictions. Interface 142 may also be used for providing diagnostic services or evaluation of the performance of various embodiments.

An embodiment of monitor interface/home telemetry portal 140 takes the form of a user interface and application, which may be embodied as a software application operating on one or more mobile computing devices, tablets, smartphones, front-end terminals in communication with back-end computing systems, laptops, or other computing devices. In an embodiment, monitor interface/home telemetry portal 140 includes a Web-based application or set of applications usable to manage user services provided by an embodiment of the invention. For example, in an embodiment, monitor interface/home telemetry portal 140 facilitates processing, interpreting, accessing, storing, retrieving, and communicating information acquired from monitor 141, EHR 160, or storage 121, including candidate diagnoses or conditions determined by embodiments of the invention as described herein. In an embodiment, monitor interface/home telemetry portal 140 sends a notification (such as an alarm or other indication) directly to user/clinician interface 142 through network 175. In an embodiment, monitor interface/home telemetry portal 140 sends a maintenance indication to provider clinician interface 142. In one embodiment of monitor interface/home telemetry portal 140, an interface component may be used to facilitate access by a user (including a clinician/caregiver or patient) to functions or information on monitor 141, such as operational settings or parameters, user identification, user data stored on monitor 141, and diagnostic services or firmware updates for monitor 141, for example.

As shown in example environment 100, in one embodiment, monitor interface/home telemetry portal 140 is communicatively coupled to monitor 141 and to network 175. In an embodiment, patient monitor 141 communicates via network 175 to computer 120 and/or provider clinician interface 142.

In an embodiment of monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient, and which may be acquired periodically or as one or more timeseries. In one embodiment, monitor 141 comprises sensors for obtaining and/or analyzing cardiac beats, which may be acquired as resting cardiac beats at at 5-10 minutes once daily, in one embodiment, such as soon after arising in the morning. In some embodiments, monitor 141 comprises patient bedside monitor, such used in hospital. In an embodiment, one or more sensor components of monitor 141 may comprise a user-wearable sensor component or sensor component integrated into the patient's environment. Examples of sensor components of monitor 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the invention disclosed herein may be received from human measurements, human observations, or automatically determined by sensors in proximity to the patient. In one embodiment, monitor 141 comprises a plethysmographic wristband sensor or wearable ECG, which may be carried out using a fitness tracker wristband device or mobile device, such as the Welch-Allyn MicroPaq™ home monitor.

Examples of physiological variables monitored by monitor 141 may also include, by way of example and not limitation, heart rate, blood pressure, oxygen saturation (SoO2), central venous pressure, other vital signs or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient in order to facilitate clinical decision making In an embodiment, a monitor such as 141 comprises a sensor probe, such as an EEG probe, and a communication link that periodically transmits identification information and probe data to patient monitor interface/home telemetry portal 140, so that the timeseries of monitored values is stored on monitor interface/home telemetry portal 140, enabling the patient manager to form a raw binary alarm indication and/or a physiological variable decision statistic. In an embodiment, patient monitor 140 collects raw sensor information, such as optical sensor 184, and performs signal processing, such as velocity measurement, forming a physiological variable decision statistic, cumulative summing, trending, wavelet processing, thresholding, computational processing of decision statistics, logical processing of decision statistics, pre-processing or signal condition, etc., part or all of which may be performed on monitor 141, monitor interface/home telemetry portal 140, interface 142, and/or computer system 120.

An embodiment of monitor 141 stores user-derived data locally or communicates data over network 175 to be stored remotely. In an embodiment, monitor interface/home telemetry portal 140 is wirelessly communicatively coupled to monitor 141. Monitor interface/home telemetry portal 140 may also be embodied as a software application or app operating on a user's mobile device. In an embodiment, monitor interface/home telemetry portal 140 and monitor 141 are functional components of the same device, such as a device comprising a sensor and a user interface. In an embodiment, monitor interface/home telemetry portal 140 is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on monitor 141 or interface 140 for performing signal conditioning of the measured patient variable(s). In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 142 operates in conjunction with software stack 125.

In embodiments, variables mapping service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages including fractal, tsoutliers, entropy, mice or similar services. In an embodiment, computation services 126 include the services or routines, which may be embodied as one or more software agents or routines such as the example embodiments of computer program routines illustratively provided in FIGS. 6A-6C. In some embodiments, computation services 126 use EHR or telemetry processing services 128, which provide services for telemetry, which mat be used for PTSD monitoring of a plurality of patients. Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
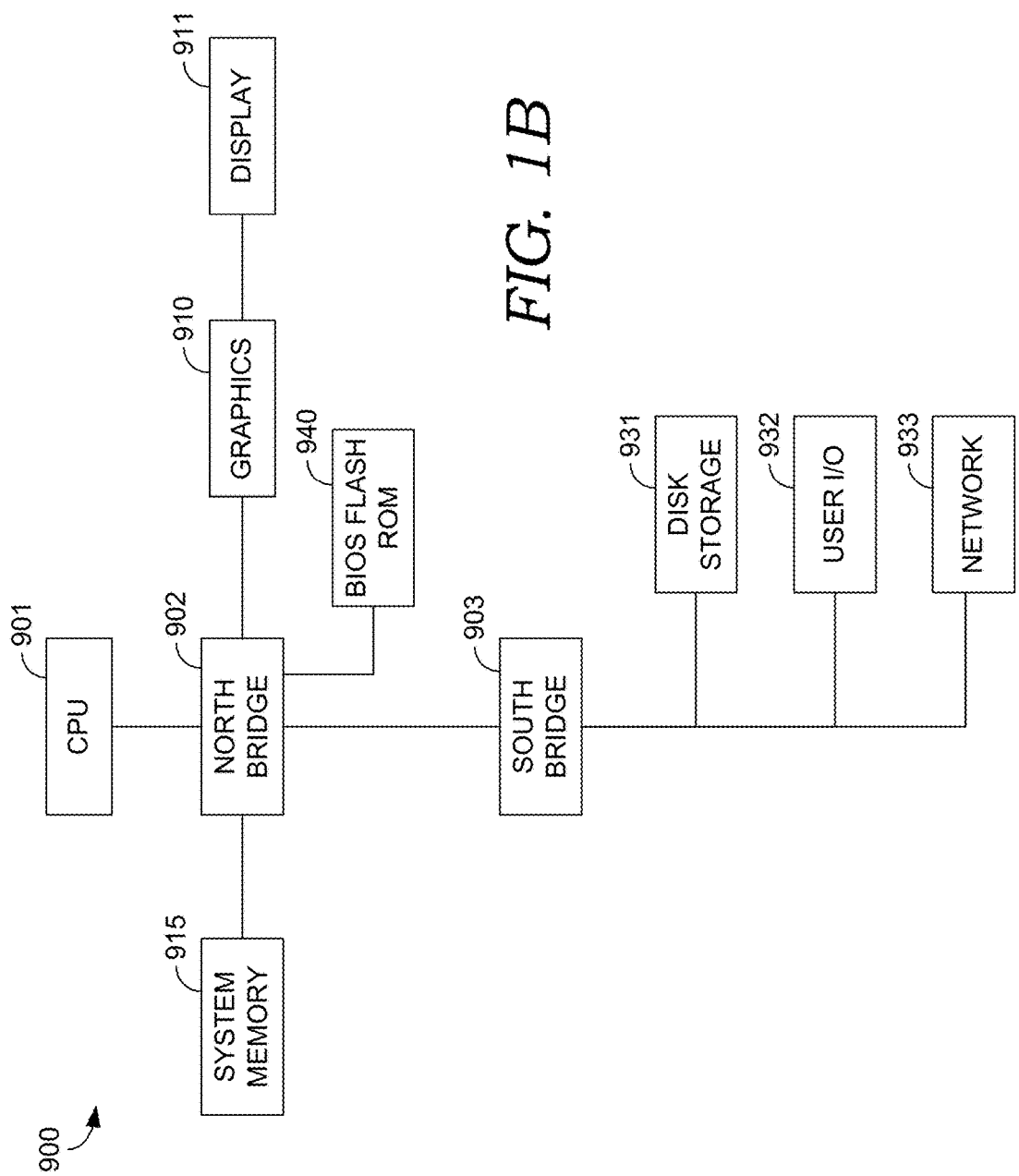

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
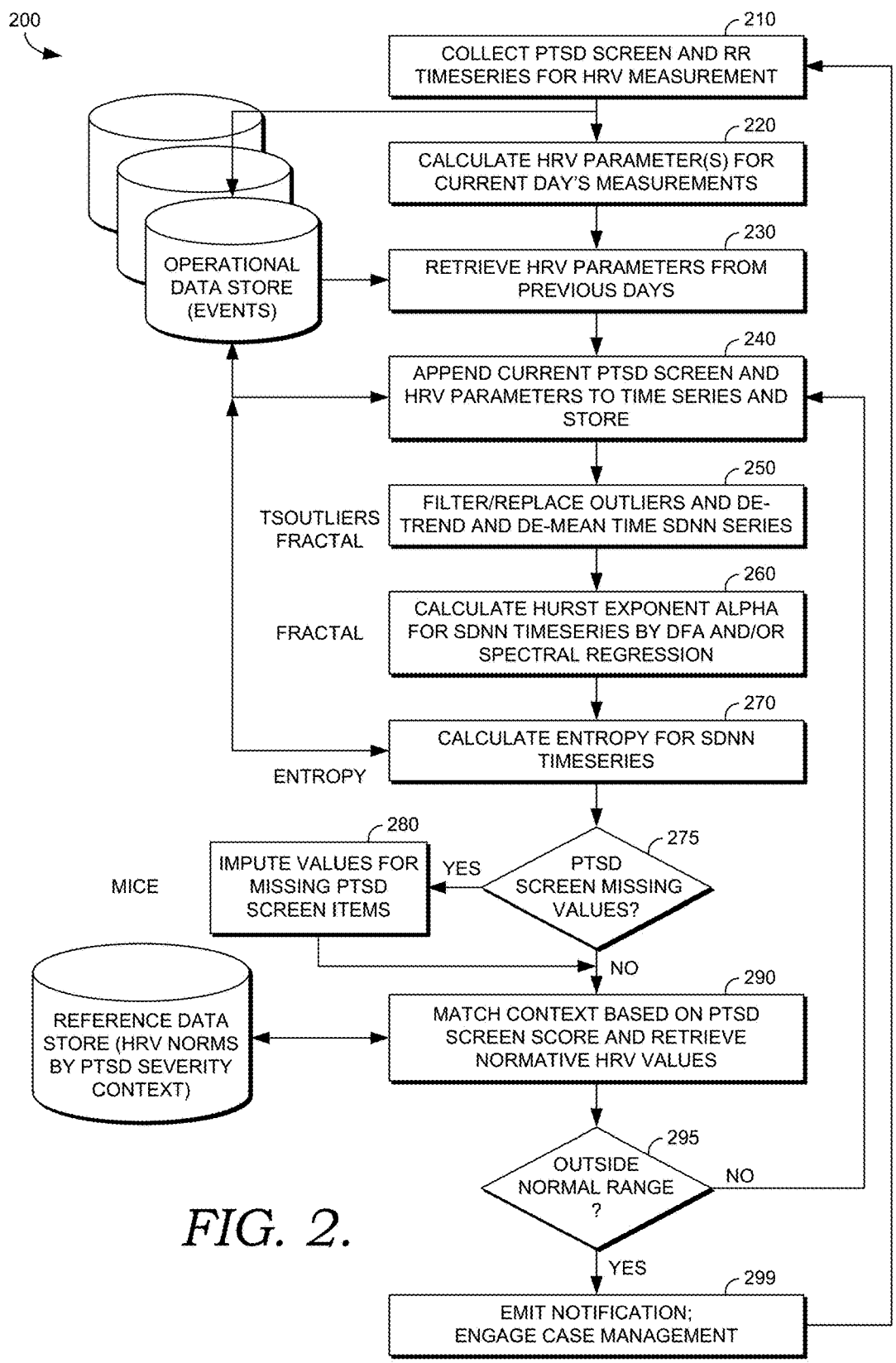
FIG. 2 depicts a flow diagram of a method for providing from context-aware PTSD monitoring to determine that a PTSD patient should receive intervention, in accordance with an embodiment of the disclosure.

Turning now to FIG. 2, an example embodiment is provided of a method 200 for context-aware PTSD monitoring to determine a person for which intervention may be needed. At a high level, method 200 comprises acquiring and processing daily HRV measurements and calculations to create one or more HRV timeseries and associating a particular subject's HRV values with an appropriate set of normative reference-range HRV values corresponding to a set of normal persons and/or PTSD patients having similar context features and survey score values. Based on a comparison of person-specific values and metrics with the reference values and metrics, determinations can be made to take some action with respect to the person. Approximate daily 5- to 10-minute RR cardiac beat timeseries may be collected, which may be de-trended and de-meaned, in some embodiments, to remove the effects of drift and location, and standard HRV parameters are calculated from each day's timeseries, including the standard deviation of NN intervals (SDNN) in seconds, average RR in seconds, and average HR in bpm. It will be appreciated that to detect and analyze the RR intervals, a series of heartbeats over a given amount of time is collected, where R is the peak of a heartbeat in a QRS complex. A plurality of days' values may be used to calculate Hurst exponent alpha, entropy, and, optionally, other metrics of scale-dependence, stationarity, nonlinearity, and chaotic properties of the multi-day timeseries. The resulting values may then be matched according to standard clinician-administered or self-reported survey instrument's scores, so as to establish context-aware normative reference values for the SDNN, Hurst exponent, entropy, and other measures. If the departure of the subject's measures from normative reference values has occurred, then the condition is deemed to be a true-positive and notification is emitted. If no departure from context-aware normative reference values has occurred then no alarm or notification is emitted.

Accordingly, at step 210, a PTSD screen or assessment and RR timeseries for HRV measurement is collected. Some embodiments of step 210 may comprise acquiring, for the subject (e.g., the patient), one or more survey instrument assessments of PTSD, such as CAPS-1 or SPAN or TSQ. Some embodiments further comprise acquiring from the subject, daily seated, resting morning RR timeseries, which may be facilitated in some embodiments by ECG or a wearable heart rate monitoring device, such as a smart watch with a suitable dual wavelength infrared plethysmographic heart rate sensor, which may need to be positioned apposed to and in direct, continuous contact with the subject's wrist skin. It will be appreciated that any suitable method for collecting a subject's heartbeat or RR timeseries may be used.

At step 220, HRV parameters for a current day's measurements are calculated. Some embodiments of step 220 comprise calculating SDNN and/or other customary HRV metrics (such as, by way of example and not limitation, power spectrum LF, HF, LF/HF ratio, RMSSD, average RR, or average HR) and storing the current day's HRV metrics. At step 230, the measurements and HRV parameters from previous days (e.g. a timeseries or previous measurement and parameters) are retrieved, for example from an operational data store, and at step 240, the current PTSD screen, the current measurements, and the current HRV parameters are appended to those corresponding from previous days, creating a current timeseries which can then be stored. At step 250, in some embodiments, outliers in the current timeseries (or SDNN timeseries) are filtered/replaced and the SDNN timeseries can be de-trended and de-meaned. In some embodiments, step 250 comprises retrieving a plurality of days' RR timeseries data, determining its stationarity by Priestley-Subba Rao test or similar means, and de-trending and/or de-mean-ing the timeseries. Some embodiments, further or alternatively comprise filtering or replacing any timeseries outliers, such as by ARIMA modeling. Some embodiments of step 250 may be facilitated using computation services 126, including the R-package tsoutliers.

At step 260, a Hurst exponent Alpha for SDNN timeseries may be calculated by detrended fluctuation analysis (DFA) and/or spectral regression. It will be appreciated that at step 260, the fractal long range correlation properties of the SDNN timeseries can be quantified. Subsequently, or in parallel, at step 270, the entropy for SDNN timeseries may be calculated. It will be appreciated that at step 270, the randomness of signals for a subject can be measured, or in other words the SDNN timeseries predictability can be assessed. Some embodiments of steps 260 and 270 may comprise determining a Hurst exponent alpha and the Shannon entropy of the de-trended SDNN timeseries. Additionally, some embodiments of step 260 may be facilitated using computation services 126, including for example the fractals and entropy R-system packages. In some embodiments, steps 250, 260, and 270 may be facilitated using a computer program routine, such as the example illustratively provided in FIGS. 6A and 6B. The metrics calculated for the SDNN timeseries may be stored in an operational data store, such as storage 121.

At step 275, a determination is made as to whether PTSD screening values are missing from the current timeseries. Some embodiments of step 275 determine whether there are any missing item-values in the most recent survey instrument for the subject. If so, at step 280 values for missing PTSD screen or assessment items may be imputed, for example, by using comparative data. In this way, it is possible to assess whether a subject is qualitatively sensitive. It may be desirable to impute data for a current subject with unbiased data values, accordingly the current subject is matched with completed reference subjects to identify appropriate reference ranges for values and obtain the one or more missing values. For example, in one embodiment, multiple imputation is performed to provide replacement values, such as by chained-equations method (i.e., Multivariate Imputation by Chained Equations, MICE), which may be facilitated using the R-systems package mice. An example computer program routine for this is illustratively shown as part of FIG. 6C. Once missing values are imputed, or alternatively if values are not missing from the collected PTSD screen (e.g. at step 210), then at step 290, a context for a subject is matched based on the subject's PTSD screening score and a PTSD severity context reference to retrieve normative values, for example normative HRV values. In one embodiment, step 290 comprises matching the current subject to similar PTSD reference context based on the completed survey score range. In this way, the context for the current subject may be calibrated, e.g. what part of the PTSD scale a current subject is in so that quality normative comparison data is retrieved. In other words, normal ranges of HRV data for subjects who have been in the same echelon are pulled and used, the matching is done based on the PTSD score of the current subject and those of the reference subjects.

At step 295, a determination is made as to whether the HRV values for the current subject are outside of the normal range retrieved by the context based matching. If not, then the method returns to step 240 to append new current data to the timeseries, or continue to monitor and acquire PTSD screen and RR timeseries for HRV measurement. If yes, then at step 299 a notification is provided, such as an alert to a caregiver or case manager, for example to engage in new case management. In particular, if the subject's SDNN Hurst exponent or SDNN entropy is abnormal compared to the context-specific normative reference ranges, then the case manage is notified, for example via electronic means or by printed report. In some embodiments, the notification may include other HRV parameters and their trends and may include summary information concerning the survey instrument score and any trend in its values, as part of the context for the case manager's review and interpretation. In some embodiments, an alert or notification may be sent to the subject, for example to one or more electronic devices including but not limited to a monitor as described above.

In an embodiment, a device for assessing a patient is provided, including subsystems comprising: a clinician-administered or self-administered survey instrument or questionnaire pertaining to signs and symptoms of stress and anxiety; a sensor for acquiring a serial cardiac physiological signals from a patient functionally connected to a programmable element; wherein the programmable elements: obtain a beat register of serial heart beats; automatically adjust the acquisition circuitry; analyze the physiological heart beat signal to provide an assessment of at least one cardiac physiologic parameter of a patient, such as the RR interval separating adjacent normal sinus rhythm heart beats; determine SDNN and other heart rate variability parameters from said beat register; quantitatively analyze and characterize the entropy and Hurst exponent of a univariate time series signal (such as serial daily SDNN values) that is the subject of PTSD decision support and filtering; compare the entropy and Hurst exponent to reference values established for individuals having survey instrument scores in a range that is comparable to the current subject's and compare the present values of the current subject to historical values determined in the subject from measurements performed on previous days.

Figure 4A:
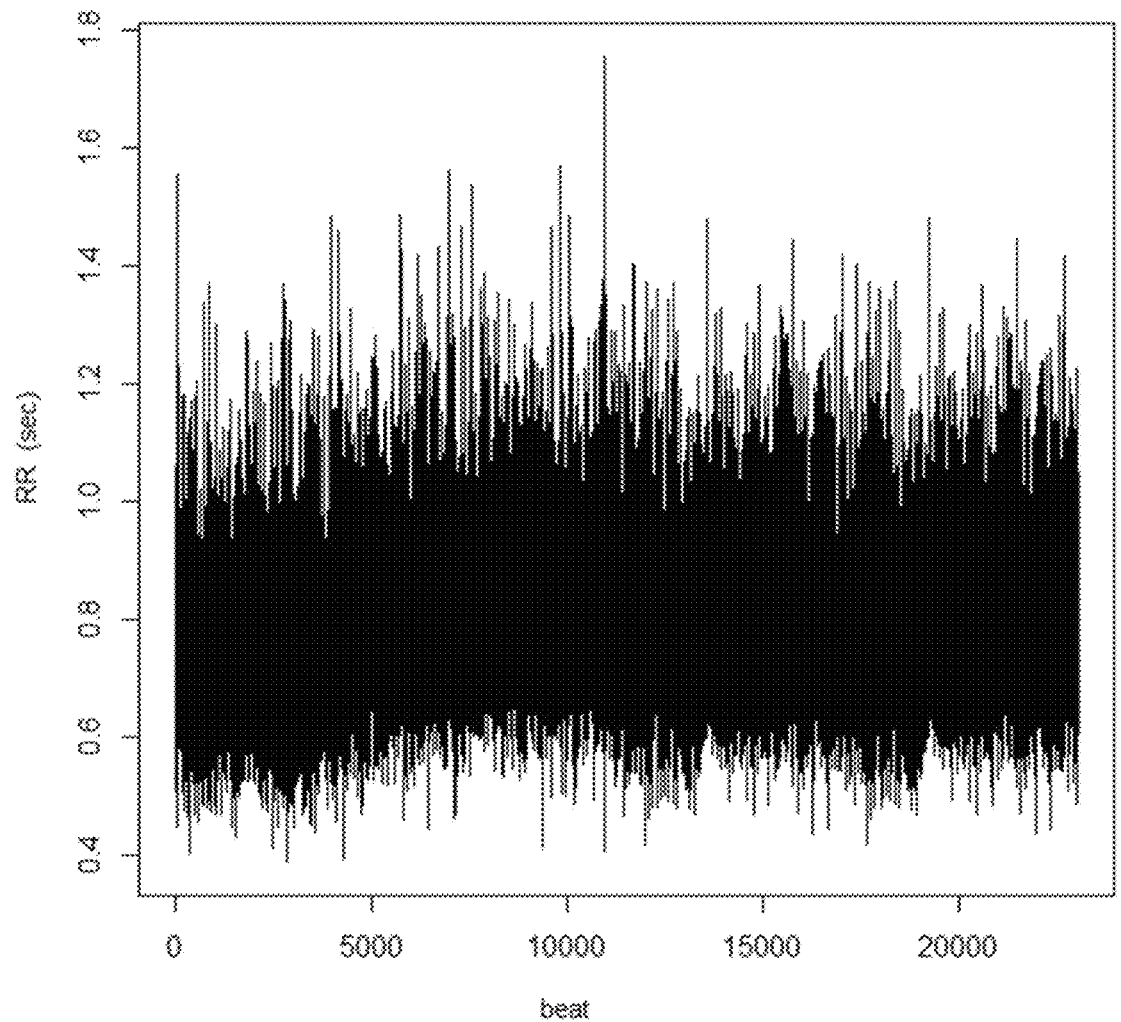
FIG. 4A-4C depict example data and analysis from a CAPS-1 assessment using heart rate variability (HRV) from a 64-day series of recordings, in accordance with an embodiment of the disclosure.
Figure 4B:
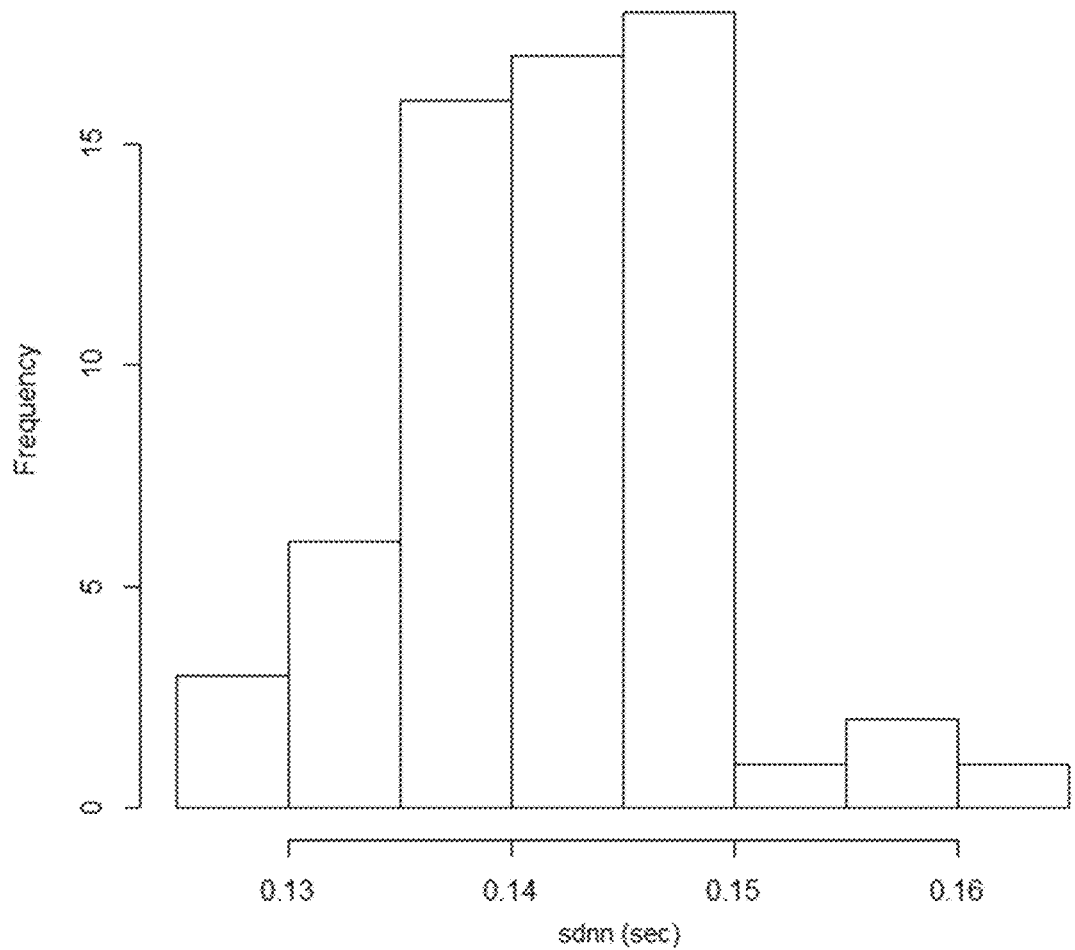
Figure 4C:
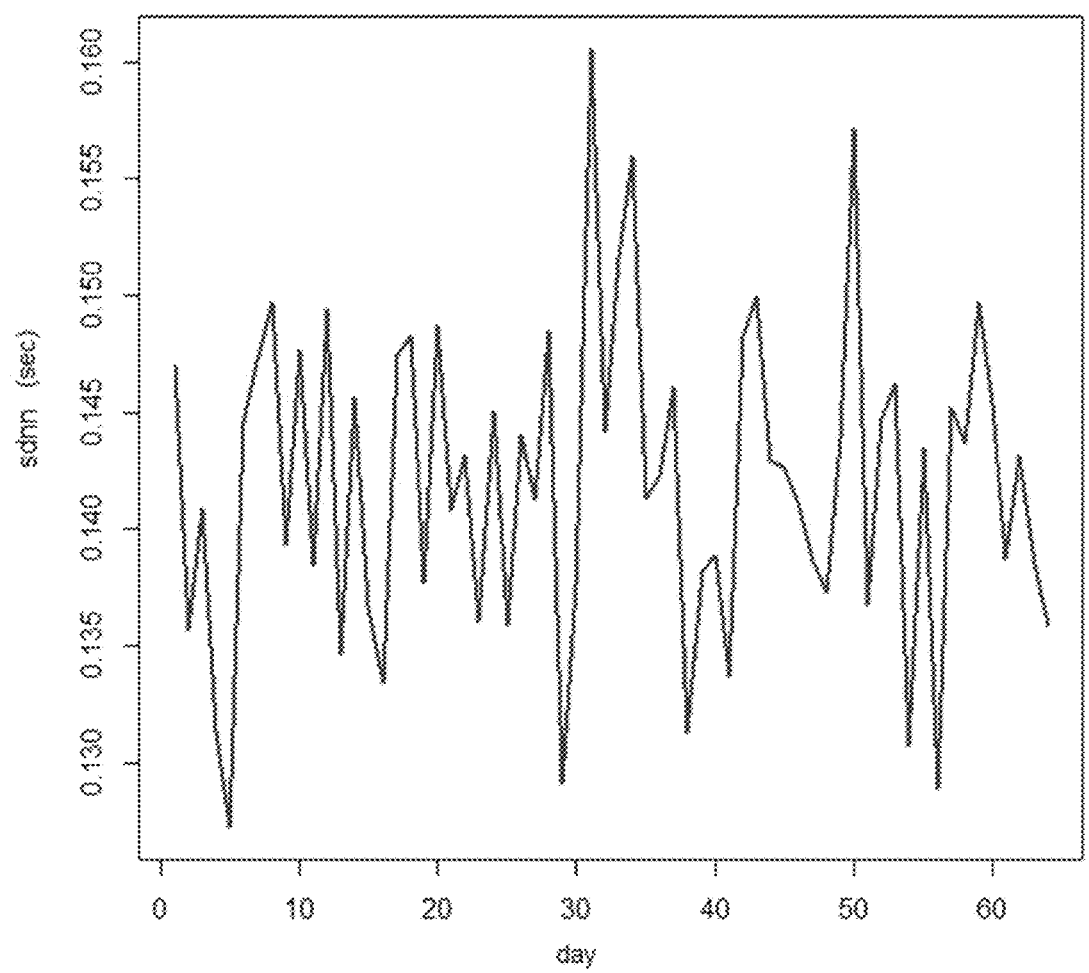

With reference to FIGS. 3-5 an example is provided of one embodiment of the invention reduced to practice for determining a Personalized Longitudinal Assessment of PTSD Severity. This example reduction to practice was accomplished using a computer running the Linux operating system, the open-source statistical software package R, and the R modules fractal, tsoutliers, entropy, and mice. In this regard, a cloud-based computing configuration is one alternative preferred embodiment of the invention. Alternatively, a stand-alone server or other computing device equipped with suitable connectivity to the device(s) by which the timeseries are acquired may likewise be utilized in another embodiment.

The term 'fractal' can be used to characterize spatial objects or temporal timeseries patterns that show a form of self-similarity over multiple powers of a base radix in spatial or temporal scale. A fractal is an entity comprised of parts that are themselves 'similar' in structure to the whole entity. The Hurst exponent is a measure of how complicated vs. simple a self-similar multi-scale object is. Modest Hurst exponent alpha <0.7 indicates a simple, monofractal structure that tends to revert to its mean; larger Hurst exponent indicates increased complexity with large-scale autocorrelations.

In this example embodiment reduced to practice, informed consent was obtained and data were acquired from a subject having moderate-to-severe PTSD, with plethysmographic sensor wristband or finger RR data provisioned with a 500 Hz sampling rate (2 ms time resolution) worn by the subject for a period of 64 days. (See e.g., FIG. 4A.) The seated, resting RR data were acquired for 5 to 10 minutes each morning in the subject's home, generally at a time between 07:00 and 08:30 a.m. The data were uploaded to the host Linux system via secure USB serial interface.

Records were selected from the subject's health records, including CAPS1 survey data. The personally-identifiable information was removed in conformance with U.S. HIPAA law and regulations, and the de-identified data were stored in a separate, secure database. Application of this example embodiment was able to determine reduced SDNN compared to the normal range, consistent with moderate-to-severe PTSD (see FIG. 5). The Hurst exponent alpha for the 64-day SDNN timeseries (see e.g., FIGS. 4B and 4C) was 0.288, indicating a briskly mean-reverting, stable process during the 64-day time interval. There was no change in the subject's workday routine or medical management during this interval, and the stability denoted by the Hurst exponent value was consistent with the case manager's impression that the subject was neither improving nor deteriorating in terms of PTSD findings during the study interval.

In an embodiment, a method and computerized system for context-aware Post Traumatic Stress Disorder (PTSD) monitoring to identify patterns of variation associated with sign and symptom changes is provided. The method and system comprising: receiving a heart-rate variability (HRV) time-series, wherein in the HRV time-series comprises a serial sequence of cardiac signals and at least one parameter associate with the HRV of a patient; deriving at least one metric for the HRV time-series, wherein the metric includes at least one of the Hurst exponent for the time-series or the entropy of the time series; associating a current PTSD screen for the patient with the HRV time-series; determining that the associated PTSD screen is complete, wherein a complete PTSD assessment includes a PTSD screen score; determining a context for the patient based on the PTSD screen score based on a set of reference PTSD screens having associated reference PTSD screen scores; retrieving, based on the context determination, a set of normative HRV value ranges, wherein the normative HRV value ranges include at least one HRV parameter and one HRV metric corresponding to the at least one parameter associated with the HRV of the patient and the derived HRV metric for the time-series; and determining, for each normative HRV value, whether the patient's corresponding HRV value is outside the retrieved normative HRV value range. It will be appreciated that if it is determined that the associated PSTD screen is incomplete, values may be imputed for missing PTSD screen items based on reference data that is similar to the data of the patient or other unbiased values. It will further be appreciated that the context for the patient can be based on any number of factors or items included in the PTSD screen. In an embodiment the context correlates to a severity of PTSD, or any other category or grouping to which the PTSD screen or PTSD screen score for a patient can be matched to a known set of reference PTSD screen data. In other words, a PTSD screen for a current patient is matched with a plurality of completed reference PTSD screens in order to identify and extract reference ranges with respect to a patient HRV time-series, associated parameter, or associated metric, in this manner a category, type, or scale of PTSD a patient is in is matched to a comparative category, type, or scale to retrieve quality normative data.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:
1. A method for context-aware Post Traumatic Stress Disorder (PTSD) monitoring to determine a person for which intervention may be needed, the method comprising:
receiving a PTSD assessment for a patient, the assessment pertaining to signs and symptoms of stress and anxiety;

acquiring, by a sensor in communication with a patient monitor, a serial sequence of cardiac signals from the patient, wherein the sequence comprises a time-based sequence of RR intervals;

generating, based on the serial sequence, a plurality of heart-rate variability (HRV) parameters corresponding to the patient;

appending the serial sequence of cardiac signals and the plurality of HRV variables to a corresponding set of previously acquired serial sequences of cardiac signals and corresponding previously generated HRV parameters thereby forming a current time-series;

calculating at least one fractal property for the time-series by applying at least one computational service to the current time series, wherein the fractal property includes at least one of the Hurst exponent for the time-series or the entropy of the time series;

determining that the received PTSD assessment is complete, wherein a complete PTSD assessment includes a PTSD survey score;

retrieving a set of normative HRV values for the patient based on a contextual match between the current PTSD assessment and a set of reference PTSD assessments, wherein the contextual match is based on the PTSD survey score;

determining, for each normative HRV value, whether a corresponding fractal property associated with the patient is outside the retrieved normative HRV value range; and based on the determining, generating a PTSD monitoring assessment for notification to a case manager.

2. The method of claim 1, further comprising: upon determination that a patient HRV value is outside the retrieved normative range for the specified HRV value emitting a notification to at least a clinician or case manager.

3. The method of claim 1, further comprising: upon a determination that the received PTSD assessment is incomplete, imputing values for the missing assessment item responses.

4. The method of claim 1 wherein the serial sequence of cardiac signals are acquired by a sensor apparatus and signal-acquisition method that utilizes heart electrocardiographic (ECG) or plethysmographic means.

5. The method of claim 1 wherein the means of acquiring and storing the serial sequence preferably is capable of a sampling rate exceeding 100 Hz for accurately determining beat location in time and the system clock possesses time resolution of at least 10 ms to record each beat.

6. The method of claim 1 wherein the PTSD assessment is at least one of a CAPS-1 score (Clinician-Administered PTSD Scale), SPAN score (Startle, Physiological arousal, Anger, and Numbness), TSQ score (Trauma Screening Questionnaire), or similar survey questionnaire instrument yielding a numeric-scale result.

7. The method of claim 3 wherein incomplete item responses in the survey are replaced by multiple imputation, preferably via chained-equation or random forest or similar means that are robust to different value-distributions of item responses.

8. The method of claim 4 wherein the score values are stratified into a plurality of numeric ranges, where each stratum denotes a grouping of subjects whose severity of PTSD- or anxiety-related signs and symptoms are approximately comparable.

9. The method of claim 4 wherein the automatic filtering and adjustment circuitry rejects premature ventricular contractions (PVCs), intervals of supraventricular tachycardia, and other arrhythmias and excludes such beats and intervals from the calculations of heart rate variability (HRV) parameters.

10. The method of claim 1 wherein one of the HRV parameters is the standard deviation of normal N-N intervals between beats (SDNN).

11. The method of claim 1 wherein each serial sequence is collected in an awake, resting individual, preferably in a seated posture, wherein each serial sequence is collected for an interval not less than 5 minutes and not greater than 10 minutes in length.

12. The method of claim 1 wherein the serial sequence is collected at a consistent time of day, such as soon after rising from bed in the morning, so as to minimize circadian variations that may affect interpretation of the HRV parameters.

13. The method of claim 1 wherein the time-series contains a plurality of daily values, preferably more than 60, so as to support numerically stable and reliable estimation of Hurst exponent and Shannon entropy.

14. The method of claim 1 wherein the estimation of Hurst exponent is performed by detrended fluctuation analysis (DFA) or spectral regression or similar means.

15. The method of claim 1 wherein the estimation of HRV parameters and Hurst exponent and Shannon entropy involves first determining time series stationarity by Priestley-Subba Rao test or similar method and de-trending and de-meaning to remove trend and location from the time series.

16. The method of claim 1 wherein the estimation of HRV parameters and Hurst exponent and Shannon entropy involves identifying any time series outlier values, preferably by a robust means such as calculating an autoregression integrated moving average (ARIMA) time series model, and wherein the estimation of HRV parameters and Hurst exponent and Shannon entropy involves filtering and replacing any time series outliers with a suitable substitute value, such as the median of the time series.

17. The method of claim 1 wherein the estimation of Shannon entropy involves discretizing the continuous-valued time series values into a plurality of bins, preferably dividing the instantiated range of values into N bins of equal width.

18. The method of claim 17 wherein the discretization binning into N bins is of a coarseness such that the number of counts in each of the bins is non-zero.

19. A method for context-aware Post Traumatic Stress Disorder (PTSD) monitoring to identify patterns of variation associated with sign and symptom changes, the method comprising:

generating a heart-rate variability (HRV) time-series, wherein in the HRV time-series includes a serial sequence of cardiac signals comprising a time-based sequence of RR intervals and at least one HRV parameter based on the HRV of a patient;

appending the HRV time-series to a plurality of corresponding previously acquired serial sequences of cardiac signals and corresponding previously generated HRV parameters thereby forming a current HRV time-series;

deriving at least one fractal property for the current HRV time-series, wherein the fractal property includes at least one of the Hurst exponent for the time-series or the entropy of the time-series;

associating a current PTSD survey for the patient with the current HRV time-series;

determining that the associated PTSD survey is complete, wherein a complete PTSD survey includes a PTSD survey score;

determining a context for the patient based on the PTSD survey score based on a set of reference PTSD surveys having associated reference PTSD survey scores;

determine, based on the context determination, a set of normative HRV value ranges, wherein the normative HRV value ranges include at least one HRV parameter and one fractal property corresponding to the at least one parameter associated with the HRV of the patient and the derived fractal property for the current time-series; and determining, for each normative HRV value, whether the patient's corresponding HRV value is outside the retrieved normative HRV value range and based on the determining, generating a PTSD monitoring assessment for notification to a case manager.

20. A computerized system comprising:

one or more processors; and computer memory storing computer-usable instructions that, when used by the one or more processors, cause the one or more processors to:

generate a heart-rate variability (HRV) time-series, wherein in the HRV time-series includes a serial sequence of cardiac signals comprising a time-based sequence of RR intervals and at least one HRV parameter derived from the HRV of a patient;

append the HRV time-series to a plurality of corresponding previously acquired serial sequences of cardiac signals and corresponding previously generated HRV parameters thereby forming a current HRV time-series;

derive at least one fractal property for the current HRV time-series, wherein the fractal property includes at least one of the Hurst exponent for the time-series or the entropy of the time-series;

associate a current PTSD screen for the patient with the HRV time-series;

determine that the associated PTSD screen is complete, wherein a complete PTSD assessment includes a PTSD screen score;

determine a context for the patient based on the PTSD screen score based on a set of reference PTSD screens having associated reference PTSD screen scores;

determine, based on the context determination, a set of normative HRV value ranges, wherein the normative HRV value ranges include at least one HRV parameter and one fractal property corresponding to the at least one parameter associated with the HRV of the patient and the derived fractal property for the current time-series; and determine, for each normative HRV value, whether the patient's corresponding HRV value is outside the retrieved normative HRV value range; and based on the determining, generate a PTSD monitoring assessment for notification to a case manager.

* * * * *

UNITED STATES PATENT AND TRADEMARK OFFICE
CERTIFICATE OF CORRECTION

PATENT NO. : 10,213,145 B1
APPLICATION NO. : 15/284463
DATED : February 26, 2019
INVENTOR(S) : Douglas S. McNair It is certified that error appears in the above-identified patent and that said Letters Patent is hereby corrected as shown below:

In the Specification

Column 01, Line 10: Please remove "Tramatic" and replace with --Traumatic--.

Column 02, Line 48: Please remove "FIG." and replace with --FIGS.--.

Column 09, Line 42: Please remove "at at" and replace with --at--.

Column 10, Line 12: Please remove "making" and replace with --making.--.

Column 11, Line 38: Please remove "mat" and replace with --may--.

Column 13, Line 50: Please remove "de-mean-ing" and replace with --de-meaning--.

Column 16, Line 27: Please remove "PSTD" and replace with --PTSD--.

Signed and Sealed this
Second Day of April, 2019

Andrei Iancu
*Director of the United States Patent and Trademark Office*